(12) United States Patent
Stahlmann

(10) Patent No.: US 7,466,147 B2
(45) Date of Patent: Dec. 16, 2008

(54) FLUID QUALITY SENSOR

(75) Inventor: Daniel Stahlmann, Huntsville, AL (US)

(73) Assignee: Continental Automotive Systems US, Inc., Auburn Hills ( * ) Notice: Subject to any disclaimer, the term of this patent is extended or adjusted under 35 U.S.C. 154(b) by 56 days.

(21) Appl. No.: 11/500,164

(22) Filed: Aug. 7, 2006

(65) Prior Publication Data

US 2007/0056365 A1    Mar. 15, 2007

Related U.S. Application Data

(60) Provisional application No. 60/706,509, filed on Aug. 8, 2005.

(51) Int. Cl.
*G01R 27/26* (2006.01)
(52) U.S. Cl. .................. 324/663; 324/670; 324/685; 324/686
(58) Field of Classification Search ........... 324/663, 324/670, 685, 686
See application file for complete search history.

(56) References Cited

U.S. PATENT DOCUMENTS

| | | | |
|---|---|---|---|
| 3,523,245 A * | 8/1970 | Lorenzino, Jr. et al. ..... 324/686 |
| 3,819,402 A | 6/1974 | Thrower, Jr. |
| 4,426,616 A | 1/1984 | Maier |
| 4,428,026 A | 1/1984 | Maltby et al. |
| 4,555,661 A | 11/1985 | Benson et al. |
| 4,915,084 A | 4/1990 | Gonze |
| 4,924,702 A | 5/1990 | Park |
| 4,945,863 A | 8/1990 | Schmitz et al. |
| 4,971,015 A | 11/1990 | Gonze |
| 5,060,619 A | 10/1991 | Sakurai et al. |
| 5,089,703 A | 2/1992 | Schoen et al. |
| 5,103,184 A | 4/1992 | Kapsokavathis et al. |
| 5,119,671 A | 6/1992 | Kopera |
| 5,134,381 A | 7/1992 | Schmitz et al. |
| 5,216,409 A | 6/1993 | Ament et al. |
| 5,230,322 A | 7/1993 | Curran et al. |
| 5,231,358 A | 7/1993 | Kapsokavathis et al. |
| 5,255,656 A | 10/1993 | Rader et al. |

(Continued)

FOREIGN PATENT DOCUMENTS

DE        4116687        11/1991

(Continued)

OTHER PUBLICATIONS

PCT International Search Report for PCT/US02/15931 mailed Aug. 26, 2002.

*Primary Examiner*—Timothy J Dole

(57) ABSTRACT

A fluid quality sensor includes a first electrode (24) that has a fluid passageway (22) that is adapted to be placed in line with at least one fluid conduit (30). A second electrode (40) is supported within the fluid passageway (22) and electrically isolated from the first electrode (24). The first electrode (24) and the second electrode (40) operate as a capacitor for making fluid quality determinations. A disclosed example includes a temperature sensor (50) thermally coupled with a mounting member (42) that supports the second electrode (40) within the first electrode 24. A disclosed example includes a multiple piece first electrode that allows for at least a portion of the second electrode (40) to be exposed and accessible near one end of at least one piece of the first electrode during a selected portion of an example assembly process.

13 Claims, 1 Drawing Sheet

U.S. PATENT DOCUMENTS

| | | | |
|---|---|---|---|
| 5,301,542 A | 4/1994 | Meitzler et al. | |
| 5,361,035 A | 11/1994 | Meitzler et al. | |
| 5,367,264 A | 11/1994 | Brabetz | |
| 5,416,425 A | 5/1995 | Mouaici | |
| 5,503,004 A | 4/1996 | Agar | |
| 5,594,163 A | 1/1997 | Suzuki | |
| 5,661,405 A | 8/1997 | Simon et al. | |
| 5,717,339 A | 2/1998 | Murphy et al. | |
| 5,861,755 A * | 1/1999 | Moerk et al. | 324/663 |
| 5,945,831 A | 8/1999 | Sargent et al. | |
| 6,057,693 A * | 5/2000 | Murphy et al. | 324/663 |
| 6,842,017 B2 | 1/2005 | McKenzie et al. | |
| 6,885,199 B2 | 4/2005 | Desmier et al. | |
| 6,927,583 B2 | 8/2005 | Vanzuilen et al. | |
| 7,030,629 B1 * | 4/2006 | Stahlmann et al. | 324/663 |
| 7,222,528 B2 | 5/2007 | Stahlmann et al. | |
| 2003/0000303 A1 | 1/2003 | Livingston et al. | |
| 2003/0117153 A1 | 6/2003 | McKenzie et al. | |
| 2004/0004487 A1 * | 1/2004 | Vanzuilen et al. | 324/663 |
| 2004/0251919 A1 | 12/2004 | Stahlmann et al. | |
| 2006/0196264 A1 | 9/2006 | Stahlman et al. | |

FOREIGN PATENT DOCUMENTS

| | | |
|---|---|---|
| DE | 19938790 A1 | 2/2001 |
| DE | 10331577 A1 | 2/2005 |
| EP | 0380752 | 8/1990 |
| EP | 0543215 | 5/1993 |
| GB | 2139766 | 11/1984 |
| GB | 2210459 A | 6/1989 |
| WO | 0227280 | 4/2002 |

* cited by examiner

FLUID QUALITY SENSOR

CROSS REFERENCE TO RELATED APPLICATIONS

This application claims priority to U.S. Provisional Application No. 60/706,509, which was filed on Aug. 8, 2005.

1. FIELD OF THE INVENTION

This invention generally relates to a sensor for determining a fluid quality. More particularly, this invention relates to a sensor that can be placed in line along a fluid flow path for determining a quality of a fluid flowing along the path.

2. DESCRIPTION OF THE RELATED ART

Various fluid quality sensors are known. One type of determination made by such sensors is the concentration of one or more components within a fluid mixture. Some example sensors use a capacitor-based measurement technique to make a determination regarding the quality of interest.

One example situation is in automotive fuel systems. It is useful, for example, to determine the alcohol content within a fuel mixture for purposes of adjusting fuel supply parameters in fuel injection systems. A known sensor for making such a determination is shown in U.S. Pat. No. 5,367,264. That document discloses a way of determining the alcohol content of a fuel mixture based on a capacitance and conductance of a capacitor-based measuring circuit, which is exposed to the fuel mixture. A variety of such devices are known.

Another situation where a fluid quality determination is useful is in a catalytic converter arrangement that uses a known selective catalytic reaction to control vehicle engine emissions. In this situation, it is useful to determine a urea concentration level in a fluid supply to the catalytic converter. Such devices utilize a mixture of urea and de-ionized water for producing ammonia hydroxide, which is used to control the nitrogen oxide in exhaust emissions. It is desirable to be able to provide an indication of a urea concentration level so that the catalytic converter will perform as needed or desired.

One shortcoming of previously proposed devices is that they are typically limited to very specific applications. Another limitation is that the placement of such devices is commonly limited to a supply or reservoir tank. There is a need for a more versatile arrangement that can accommodate various situations and that can be more readily incorporated into an appropriate system. Another challenge has been to achieve an adequate temperature measurement including a sufficiently rapid response time. There is a need for an improved temperature sensing feature. This invention addresses those needs.

SUMMARY OF THE INVENTION

One exemplary sensing device for detecting a fluid property includes a first electrode having a fluid passageway extending through at least a portion of the first electrode. A second electrode cooperates with the first electrode to function as a capacitor. A mounting member is secured to the second electrode and has a portion supported by the first electrode. The mounting member supports the second electrode within the first electrode fluid passageway such that fluid in the passageway can fill a space between the first and second electrodes. A temperature sensor is thermally coupled with the mounting member such that the temperature sensor obtains a temperature indication from fluid contacting a portion of the mounting member within the fluid passageway.

One example first electrode comprises at least two distinct portions that are at least initially separate pieces. The mounting member and the second electrode are at least partially received within one of the portions. At least some of the second electrode is accessible near an end of the one portion within which the second electrode is at least partially received. In one example, when the first electrode portions are subsequently secured together, the second electrode is completely contained within the first electrode.

In one example the second electrode at least temporarily extends beyond an end of a portion of the first electrode. An example assembly technique includes applying a force to the second electrode by accessing the exposed portion. Applying a force provides for confirming that the mounting member and second electrode are securely positioned together relative to the first electrode before the device is assembled into a fluid supply system.

The various features and advantages of this invention will become apparent to those skilled in the art from the following detailed description. The drawings that accompany the detailed description can be briefly described as follows.

DETAILED DESCRIPTION OF THE PREFERRED EMBODIMENT

Figure 1:
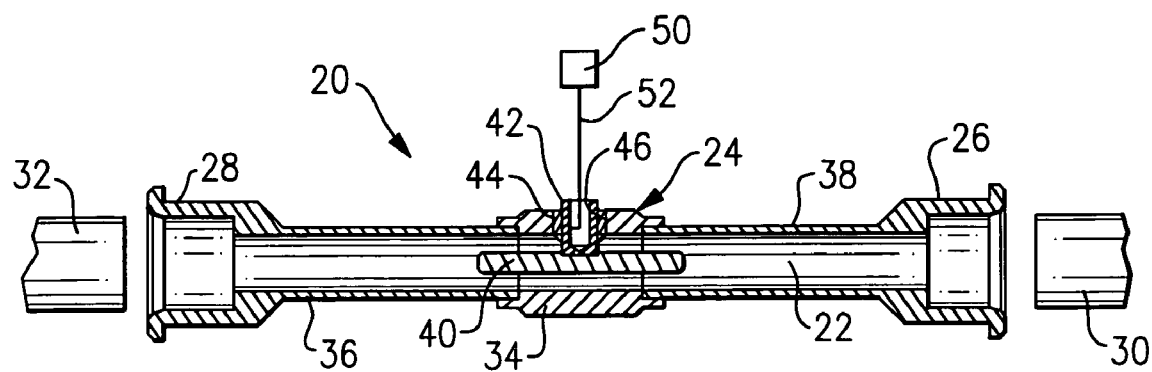
FIG. 1 is a cross-sectional illustration showing an example embodiment of a sensor designed according to this invention.

As can be appreciated from FIG. 1, a fluid quality sensor device 20 has a fluid passageway 22 through which a fluid of interest can flow. The fluid passageway 22 is formed through a first electrode 24. A first end 26 and a second end 28 of the first electrode 24 are adapted to be coupled with at least one fluid conduit 30. In the illustrated example, the first end 26 can be coupled with a first conduit 30 and the second end 28 can be coupled with a second conduit 32. In one example, the conduits 30 and 32 are sections of the same conduit.

By coupling the first electrode 24 with the conduits 30 and 32, the fluid passageway 22 accommodates fluid flowing through the conduits 30 and 32 and is in line with the conduits of an appropriate portion of a fluid handling system. In one example, the conduits 30 and 32 are fuel supply lines. In another example, the conduits 30 and 32 are a urea mixture supply for a catalytic converter arrangement.

In the illustrated example, the first electrode 24 comprises distinct pieces that are assembled together to form the entire first electrode 24. In this example, a first piece 34 is a central portion of the first electrode 24. A second piece 36 completes one end of the first electrode 24 while a third piece 38 completes another end. The individual pieces of the first electrode 24 are secured together to provide electrical continuity along the entire first electrode 24 and to establish a fluid-tight seal at the interfaces between the distinct pieces.

A second electrode 40 is supported within the fluid passageway 22 such that fluid flowing through the passageway 22 fills spacing between the inside of the first electrode 24 and the exterior of the second electrode 40. In the example of FIG. 1, the second electrode 40 comprises a solid rod. In another example, the second electrode 40 comprises a hollow tube. In such an example, the second electrode 40 includes a second fluid passageway through which the fluid flowing in the passageway 22 may flow.

The example of FIG. 1 is useful in situations where the fluid of interest has a relatively high conductivity such as a urea concentration fluid sensor, for example. Examples having a hollow tube second electrode 40 are useful in situations including a fluid of lower conductivity such as an automotive fuel alcohol concentration sensor, for example. Given this description, those skilled in the art will be able to select appropriate configurations of the second electrode 40 and size it according to a size of the first electrode 24 to meet the needs of their particular situation.

The first electrode 24 and the second electrode 40 operate as a cathode and an anode of a capacitor, respectively. Capacitor-based fluid quality or property measurement techniques are known.

The illustrated second electrode 40 is supported within the fluid passageway 22 by a mounting member 42 that has a first end secured to the second electrode 40 and another portion supported by the first electrode 24. In one example, one end of the mounting member 42 is brazed to the second electrode 40. In another example, the mounting member and the second electrode are made from a single piece of material. An insulator 44 electrically isolates the mounting member from the first electrode 24 and, therefore, the second electrode 40 remains electrically isolated from the first electrode 24. In the event that fluid fills the passageway 22, the fluid between the first electrode 24 and the second electrode 40 builds a dielectric for capacitor-based fluid quality measurements. By operating the capacitor comprising the first electrode 24 and second electrode 40 in a desired manner, the fluid quality of interest can be determined. In one example, the sensor electronics (not illustrated) use known techniques for making such a determination.

In the example of FIG. 1, the mounting member 42 comprises a partially hollow cylinder and the insulator 44 comprises a glass seal, which serves the dual function of supporting the mounting member 42 in an electrically isolated manner from the first electrode 24 and providing a fluid-tight seal of an opening 46 in the first electrode 24 through which the mounting member 42 is at least partially received.

Another feature of the embodiment of FIG. 1 is a temperature sensor 50. In this example, the temperature sensor 50 comprises a known NTC device and is thermally coupled with the mounting member 42 through a suitable lead 52. This arrangement allows for detecting temperature of fluid in the passageway 22 that is in contact with the mounting member 42. The temperature information can be used as known for making fluid quality determinations.

Figure 2:
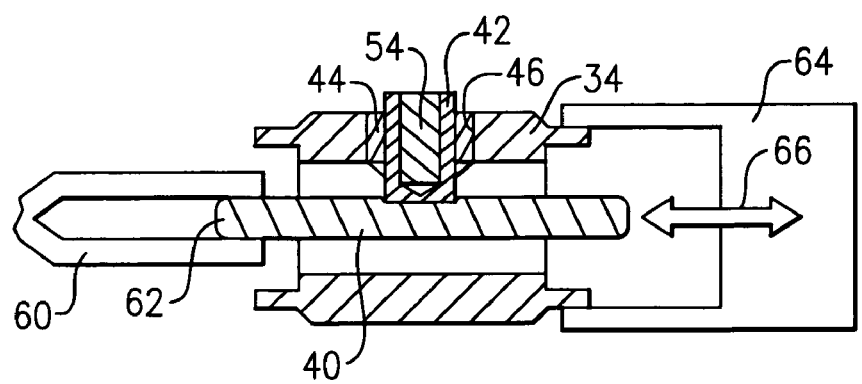
FIG. 2 illustrates a selected portion of an assembly process useful for making the embodiment of FIG. 1.

As can best be appreciated from FIG. 2, an example mounting member 42 has a generally cylindrical exterior that is at least partially hollow. In the illustrated example, the interior is at least partially filled with a thermal interface material 54. In such an example, the temperature sensor 50 is thermally coupled with the thermal interface material 54. Having the temperature sensor associated with the mounting member allows for better temperature determinations compared to previous designs. By obtaining a temperature reading based upon fluid contact with the mounting member 42 within the fluid passageway 22 allows for more accurate and faster temperature response of a temperature sensor 50. This unique arrangement of a temperature sensor and mounting member provides superior temperature capabilities compared to previous arrangements.

In one example, the mounting member 42 is selected to have an outside dimension that causes an increased dimension for the insulating member 44 compared to previous designs. When a glass seal is used for the insulating member in such an example, an increased diameter results in a glass seal that can withstand higher burst pressures and is more tolerant to freeze cycles compared to previous arrangements.

FIG. 2 schematically illustrates a selected portion of an example assembly process useful for making the embodiment of FIG. 1. The first piece 34 of the first electrode 24, the second electrode 40 and the mounting member 42 are assembled together as schematically shown. In this example, at least a portion of the second electrode 40 is exposed near at least one end of the first piece 34. In the illustrated example, the second electrode 40 has a length that is greater than a length of the first piece 34. In the illustrated example, both ends of the second electrode 40 protrude beyond the ends of the first piece 34.

Leaving an exposed or accessible portion of the second electrode 40 allows for a test to confirm a secure connection between the mounting member 42 and the second electrode 40 on the one hand and a secure positioning of them within the first piece 34 on the other hand.

In the example of FIG. 2, a gripper 60 grasps one end 62 of the second electrode 40 while a holder 64 grasps the first piece 34. Movement of the gripper 60, the holder 64 or both allows for applying a force as schematically shown at 66 in either direction to effectively push, pull or both on the second electrode 40 relative to the first piece 34. Using an appropriate force allows for testing whether an appropriate connection has been made so that the second electrode 40 will be securely maintained in a desired position within the fluid passageway 22.

In one example, the gripper 60 and the holder 64 are part of an automated testing machine. In another example, an individual's fingers serve as the gripper 60 and the holder 64. Making the first electrode 24 of individual pieces 34, 36 and 38 allows for testing the security of the second electrode 40 within the fluid passageway 22 prior to completing the first electrode 24 and eventually inserting the sensor device 20 within a fluid handling system.

In the illustrated example, once an appropriate test confirms the security of the second electrode 40 within the fluid passageway 22, the second piece 36 and third piece 38 are assembled together with the first piece 34 for making the entire first electrode 24. In the illustrated example, the overall length of the first electrode 24 is greater than the overall length of the second electrode 40 when the device is completely assembled.

The illustrated example sensor 20 can be readily incorporated into a fluid supply arrangement and made part of a fuel supply line, for example. In one example, one end of the first electrode 24 is secured to a tank or reservoir while the other end is secured to a conduit that allows fluid to flow into or out of the tank or reservoir.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

I claim:

1. A sensor device for detecting a fluid property, comprising:
   a first electrode having a fluid passageway through at least a portion of the first electrode;
   a second electrode that cooperates with the first electrode to function as a capacitor;

an electrically conductive mounting member secured to the second electrode and having a portion supported by the first electrode, the mounting member supporting the second electrode within the first electrode fluid passageway such that fluid in the passageway can fill a space between the first and second electrodes; and a temperature sensor directly thermally coupled with the mounting member such that the temperature sensor obtains a temperature indication from fluid that contacts a portion of the mounting member within the fluid passageway.

2. The device of claim 1, wherein the first electrode has a central portion having a first length and the second electrode has a second length longer than the first length such that at least a portion of the second electrode protrudes beyond at least one end of the first electrode central portion.

3. The device of claim 2, wherein the first electrode comprises at least one other portion connected to the central portion and having a length such that a combined length of the central portion and the at least one other portion is at least as long as the second length.

4. The device of claim 1, wherein the mounting member includes
a thermal interface material and wherein the temperature sensor contacts at least the thermal interface material.

5. The device of claim 1, wherein the mounting member is at least partially transverse to the second electrode.

6. The device of claim 5, wherein the mounting member is generally perpendicular to the second electrode.

7. The device of claim 1, including an insulator electrically isolating the mounting member from the first electrode.

8. The device of claim 7, wherein the insulator comprises a glass seal.

9. A sensor device for detecting a fluid property, comprising:
a first electrode having a fluid passageway through at least a portion of the first electrode;
a second electrode that cooperates with the first electrode to function as a capacitor;
a mounting member secured to the second electrode and having a portion extending at least partially through an opening in the first electrode, the opening being transverse to the fluid passageway, the mounting member supporting the second electrode within the first electrode fluid passageway such that fluid in the passageway can fill a space between the first and second electrodes;
an insulator between the mounting member and the opening in the first electrode, the insulator electrically isolating the mounting member from the first electrode; and
a temperature sensor directly thermally coupled with the mounting member such that the temperature sensor obtains a temperature indication from fluid that contacts a portion of the mounting member within the fluid passageway.

10. The device of claim 9, wherein the insulator comprises a glass seal.

11. A sensor device for detecting a fluid property, comprising:
a first electrode having a fluid passageway through at least a portion of the first electrode;
a second electrode that cooperates with the first electrode to function as a capacitor;
a mounting member secured to the second electrode and having a portion supported by the first electrode, the mounting member supporting the second electrode within the first electrode fluid passageway such that fluid in the passageway can fill a space between the first and second electrodes; and
a temperature sensor directly thermally coupled with the mounting member such that the temperature sensor obtains a temperature indication from fluid that contacts a portion of the mounting member within the fluid passageway, the temperature sensor being isolated from fluid within the fluid passageway.

12. The device of claim 11, wherein the mounting member is at least partially hollow and an interior of the mounting member is at least partially filled with a thermal interface material, the temperature sensor being thermally coupled with the thermal interface material.

13. A sensor device for detecting a fluid property, comprising:
a first electrode having a fluid passageway through at least a portion of the first electrode;
a second electrode that cooperates with the first electrode to function as a capacitor;
a mounting member secured to the second electrode and having a portion supported by the first electrode, the mounting member supporting the second electrode within the first electrode fluid passageway such that fluid in the passageway can fill a space between the first and second electrodes, the mounting member being at least partially hollow and including a thermal interface material at least partially filling an interior of the mounting member; and
a temperature sensor thermally coupled with the thermal interface material such that the temperature sensor obtains a temperature indication from fluid that contacts a portion of the mounting member within the fluid passageway.

* * * * *